United States Patent [19]
Harandi et al.

[11] Patent Number: 5,144,086
[45] Date of Patent: Sep. 1, 1992

[54] ETHER PRODUCTION

[75] Inventors: Mohsen N. Harandi; Werner O. Haag, both of Lawrenceville; Hartley Owen, Belle Mead; Weldon K. Bell, Pennington, all of N.J.

[73] Assignee: Mobil Oil Corporation, Fairfax, Va.

[21] Appl. No.: 695,843

[22] Filed: May 6, 1991

[51] Int. Cl.⁵ .................................................. C07C 41/09
[52] U.S. Cl. ...................................... 568/698; 568/897
[58] Field of Search .............................. 568/698, 897

[56] References Cited

U.S. PATENT DOCUMENTS

| | | | |
|---|---|---|---|
| 4,042,633 | 8/1977 | Woods | 260/614 R |
| 4,423,271 | 12/1983 | Obenaus et al. | 585/639 |
| 4,857,664 | 8/1989 | Huang et al. | 568/698 |
| 4,967,020 | 10/1990 | Marler et al. | 568/897 |
| 4,969,987 | 11/1990 | Le et al. | 208/67 |

Primary Examiner—Howard T. Mars
Assistant Examiner—Kimberly J. Kestler
Attorney, Agent, or Firm—Alexander J. McKillop; Charles J. Speciale; Jessica M. Sinnott

[57] ABSTRACT

A process for synthesizing di-isopropyl ether (DIPE) by etherification of isopropanol. A multi-stage process can employ propene in mixture with other feedstock materials, such as propane from refinery gas, in a primary hydration stage to produce isopropanol. The isopropanol is enriched between stages to remove water. In the second reaction stage the isopropanol is converted catalytically with large pore acidic zeolite to yield DIPE, which can be separated to recover pure propene.

16 Claims, 3 Drawing Sheets

ETHER PRODUCTION

FIELD OF THE INVENTION

This invention relates to production of di-isopropyl ether (DIPE) from $C_3+$ olefinic feedstocks. Particularly, the invention relates to a novel technique for utilizing propene-containing hydrocarbon streams in a multistage process for synthesizing, recovering and decomposing isopropanol to produce DIPE and pure propene.

BACKGROUND OF THE INVENTION

The need to eliminate lead-based octane enhancers in gasoline has provided incentive for development of processes to produce high octane gasolines blended with lower aliphatic alkyl ethers as octane boosters. Supplementary fuels are being vigorously developed in the petroleum refining industry. Lower molecular weight alcohols and ethers such as isopropyl alcohol (IPA), isopropyl t-butyl ether (IPTBE), and diisopropyl ether (DIPE) are in the boiling range of gasoline fuels and are known to have a high blending octane number. They are useful octane enhancers. In addition, by-product propene (propylene) from which IPA and DIPE can be made is usually available in a fuels refinery, typically as a $C_3+$ aliphatic stream rich in propene and propane. The petrochemicals industry also produces mixtures of light olefin streams in the $C_2$-$C_7$ molecular weight range and the conversion of such streams or fractions thereof to alcohols and/or ethers can also provide products useful as solvents and blending stocks for gasoline.

Catalytic hydration of olefins to provide alcohols and ethers is established technology for production of the IPA and DIPE and is of significant commercial importance. Representative olefin hydration processes are disclosed in U.S. Pat. Nos. 4,334,890 (Kochar); 3,912,463 (Kozlowski et al.); 4,042,633 (Woods); 4,499,313 (Okumura et al.); 4,886,918 (Sorensen et al).

Olefin hydration employing medium pore and large pore zeolite catalyst is a known synthesis method. As disclosed he corresponding alcohol, essentially free of ether and hydrocarbon by-product. Acid resin catalysts such as "Amberlyst 15" may also be used for hydration of light olefins.

Production of ether from secondary alcohols such as isopropanol and light olefins is known. As disclosed in U.S. Pat. No. 4,182,914 (Imaizumi), DIPE is produced from IPA and propylene in a series of operations employing a strongly acidic cation exchange resin as catalyst. Recently, processes for the direct hydration of olefins to provide alcohols and ethers using medium pore shape selective metallosilicate zeolite catalyst, such as zeolite Beta have been disclosed in U.S. Pat. No. 4,857,664 (Huang et al.), incorporated by reference.

Adapting available refinery feedstock to produce these oxygenates simultaneously as octane enhancers can involve two different olefin hydration and etherification processes, i.e. propene hydration-etherification to give DIPE and IPA. Accordingly, a challenge is provided to explore these processes to discover how they may be integrated in a manner more beneficial to the production of high octane gasoline.

It is a main object of this invention to provide a process for production of ethers from lower olefin feedstock. It is another object of the present invention to provide an integrated process for the production of isoproanol and di-isopropyl ether in a continuous process, incorporating novel multi-stage reactor, product separation and fractionation techniques. A further object is to provide for conversion of isopropanol to di-isopropyl ether and propene.

SUMMARY OF THE INVENTION

An integrated continuous process has been discovered for the production of di-isopropyl ether and substantially pure propene from a mixed aliphatic feedstock containing propene and propane, comprising the steps of: contacting the aliphatic feedstock and water in a first hydration zone with acidic olefin hydration catalyst under olefins hydration conditions whereby an effluent stream containing isopropanol and unreacted aliphatic hydrocarbon is produced substantially free of di-isopropyl ether; separating the hydration zone effluent stream to recover unreacted hydrocarbon and an oxygenate stream comprising isopropanol; contacting said isopropanol oxygenate stream with a zeolite acidic etherification catalyst in a second reaction zone under to produce an etherification effluent stream containing di-isopropyl ether, water and propene; and fractionating the etherification effluent stream to produce a substantially pure propene product stream and an ether product stream. In the preferred embodiment the process includes a fractionation step for separating a $C_3$- unreacted hydrocarbon overhead fraction from an isopropanol-rich aqueous bottoms stream and further fractionating the isopropanol-rich aqueous stream to provide an azeotropic mixture of isopropanol and water, which is contacted with etherification catalyst consisting essentially of zeolite Beta. A novel process step is provided for production of diisopropyl ether and propene from isopropanol feed wherein isopropanol containing 0–20 wt % water is contacted with acidic large pore zeolite etherification catalyst under etherificaton conditions to convert at least 60% of the isopropanol to di-isopropyl ether, water and propene.

DETAILED DESCRIPTION OF THE INVENTION

In the preferred embodiment of the instant invention the principal components of known processes are integrated in a manner providing a highly advantageous and surprising advancement in refinery technology leading to the production of high octane gasoline blending components. Known processes are combined in a unique configuration that provides enhancement of the performance of component processes as well as achieving surprising advantages for the integrated process. The processes integrated include olefin hydration and etherification to produce alcohol and ether.

The process of the present invention is directed to maximizing the utilization of $C_3+$ refinery streams for the production of those gasoline range oxygenated species, or oxygenates, known to exhibit high octane numbers which are useful for gasoline product blending.

Figure 1:
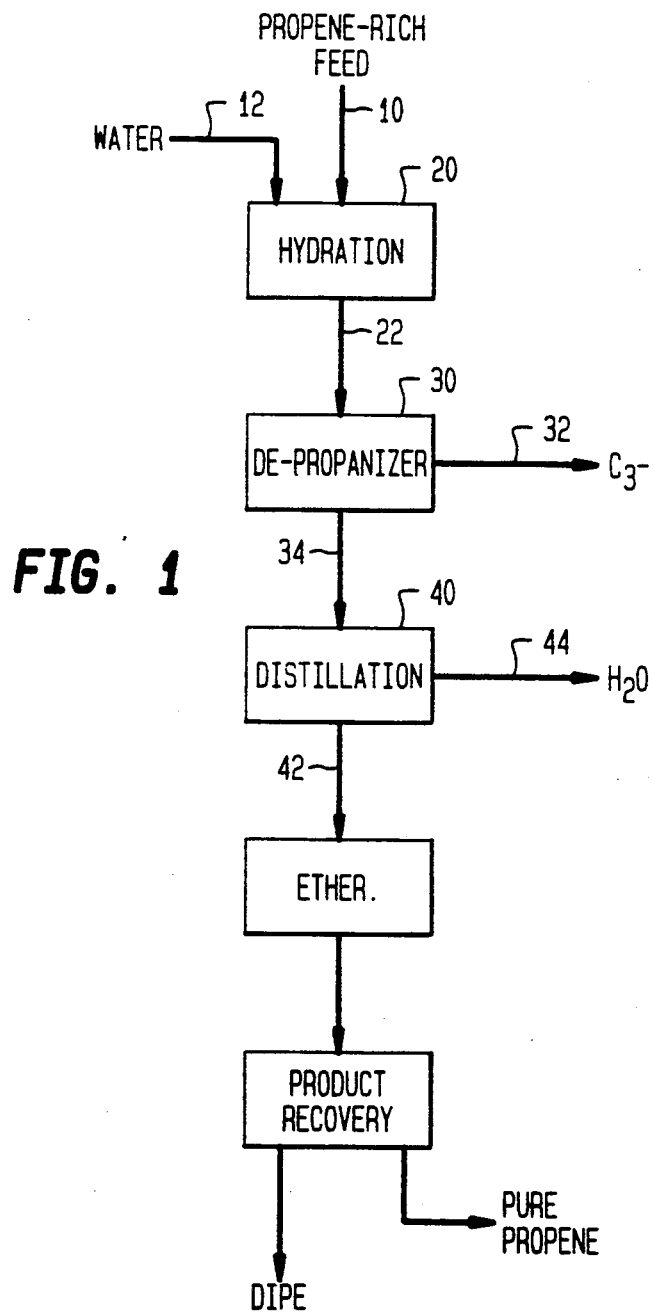
FIG. 1 is a schematic flow diagram of the integrated process of this invention, depicting the major unit operations operatively connected in a continuous plant.

Referring now to FIG. 1, a schematic process flow diagram according to this invention depicts the major unit operations of the process. A propene-rich feedstream 10 is introduced along with a stoichiometric excess of water from stream 12 to a primary hydration reactor section 20, and a first reaction effluent stream 22 is recovered for separation in depropanizer means 30 wherein propane and unreacted C3-volatile components are removed in an overhead stream 32 to recover isopropanol in an aqueous stream 34. This aqueous stream is further separated by distillation means 40 to provide an IPA-rich overhead azeotrope stream 42 and byproduct water 44, which may be recycled with makeup water feedstream 12. The isopropanol-rich aqueous bottoms stream 34 from depropanizer unit 30 is preferably fractionated to provide an azeotropic mixture consisting essentially of about 85 wt % isopropanol and about 15 wt % water. It is understood that various unit operations may be employed to enrich the isopropanol and remove water from the primary reaction effluent. The preferred apparatus employed for the integrated continuous process for the production of diisopropyl ether and substantially pure propene from mixed aliphatic feedstock includes: a) primary reactor means for contacting the aliphatic feedstock and water in a first hydration zone with acidic olefin hydration catalyst under olefins hydration conditions whereby an effluent stream containing isopropanol and unreacted aliphatic hydrocarbon is produced substantially free of di-isopropyl ether; b) means for separating the hydration zone effluent stream to recover unreacted hydrocarbon and isopropanol (The fractionation unit 30 for separating the C3-unreacted hydrocarbon overhead fraction is typically a depropanizer column.); c) second reactor means for contacting the isopropanol stream with a zeolite acidic etherification catalyst in a second reaction zone under etherification condition to produce an etherification effluent stream containing di-isopropyl ether, water and propene; and d) fractionatiion means for receiving the etherification effluent stream to produce a substantially pure propene product stream and an ether product stream. The product fractionation may be a distillation tower recovering propene overhead followed by further distillation of the DIPE-water bottoms to recover a dry ether product.

The preferred primary stage hydration catalyst comprises ZSM-5 or polysulfonic acid resin and produces oxygenate containing isopropanol. The olefins hydration and etherification process integrated in the present invention employs the reaction of propylene with water catalyzed by strong acid to form isopropanol. Reaction may be allowed to continue in the hydration zone to form di-isopropyl ether; however, it is advantageous to maximize the isopropanol yield in the primary hydration reaction stage to provide alcohol-rich feed for the subsequent etherification stage. The operating conditions of the olefin hydration step include a temperature of about 50° to 450° C., pressure of about 700 to 24000 kPa (100 to about 3500 psi), and a water to olefin mole ratio of about 0.1 to 30, preferably 0.3-5. Details of a process for selective isopropanol synthesis are given in U.S. Pat. No. 4,214,107 (Chang et al.) empoying a crystalline aluminosilicate zeolite catalyst having a silica to alumina ratio of at least 12 and a Constraint Index of from 1 to 12, e.g., acidic ZSM-5 type zeolite. Olefin hydration to provide mixtures of DIPE and isopropyl alcohol (IPA) is described in U.S. Pat. Nos. 4,214,107; 4,499,313 and pending U.S. application Ser. No. 336,582 filed 10 Apr. 1989 by Bell et al. The preferred catalytic methods for making IPA employ solid acid catalysts, such as zeolite ZSM-5 aluminosilicate. Hydration reaction conditions may vary widely in choice of temperature, pressure and reaction time. The olefin hydration process of this invention can be carried out under liquid phase, vapor phase, supercrital dense phase, or mixtures of these phases in semi-batch or continuous manner using a stirred tank reactor or fixed bed flow reactor. Reaction times of from about 20 minutes to about 20 hours when operating in batch and a LHSV of from about 0.1 to about 10 when operating continuously are suitable. It may be feasible to recover any unreacted olefin and recycle it to the reactor.

The second stage process reaction step for production of diisopropyl ether and propene from the isopropanol-rich stream comprises contacting isopropanol containing 0–20 wt % water with acidic large pore zeolite etherification catalyst under etherificaton conditions to convert at least 60% of the isopropanol to di-isopropyl ether, water and propene. Preferably this process step is conducted under conditions wherein the second reaction stage feedstream contains at least 80 wt % isopropanol contains not more than about 15 wt % water and wherein etherification reaction temperature is about is maintained in the range of 90°–200° C. (optimum about 160° C.). It is advantageous to employ isopropanol reactant comprising an azeotropic mixture consisting essentially of about 85 wt % isopropanol and about 15 wt % water. Typically, the second reacton stage is followed by the step of fractionating etherification reaction effluent to recover substantially pure propene and DIPE streams. By operating the second reaction stage as a continuous process at least 60% of the isopropanol is converted to di-isopropyl ether, water and propene with about 30 to 90% approach to equilibrium. This reaction is optimized with substantially anhydrous isopropanol feedstream containing not more than about 15 wt % water; wherein etherification reaction temperature is about 160° C., space velocity is about 10 to 20 WHSV. Reaction pressure may be varied considerably, usually over the range of about 450–9000 kPa (50–1200 psig), preferably about 450 to 7000 kPa (200–1000 psig).

The preferred etherification catalyst consists essentially of acidic aluminosilicate zeolite Beta having a silica:alumina ratio of about 30:1 to 50:1 and alpha value of about 200 to 1000. It is understood that zeolite Beta can be synthzised with aluminum, boron, gallium or iron tetrahedrally coordinated to provide Bronsted acid sites in the metallosilicate framework. Zeolite Beta has ten-membered rings forming pores of about 7.5A°. Other large pore zeolites useful in converting isopropanol include zeolite Y and NU-2. The reaction may be conducted in a fixed catalyst bed reactor, ebullated bed, slurry reactor, fluiized bed, etc , within the skill of the art. While liquid phase reaction at elevated pressure is preferred, dense phase or gaseous reactions can be used. While second reaction stage feed may consist essentially of anhydrous isopropanol, inert diluents may be employed to promote gas/liquid contact. For instance, pentane or other C4–C6 paraffins or cycloaliphatics may be employed. Olefins other than propene are not ordinarily tolerated, since C4+ alkenes are reactive to produce byproduct ethers. DIPE is tolerated in the second stage feed.

It has been found that water strongly influences the activity of zeolite Beta for synthesis of DIPE from IPA.

Figure 2:
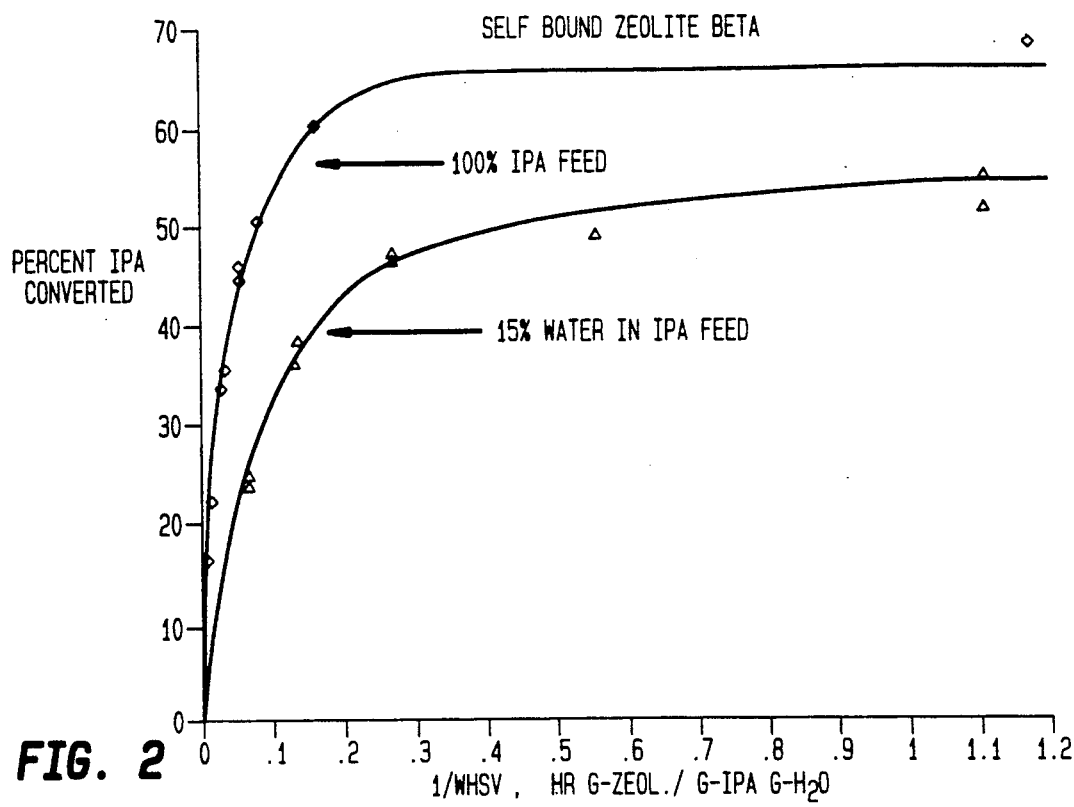
FIGS. 2, 3 and 4 are graphic plots of isopropanol (IPA) conversion, showing effects of water, space velocity and different catalytic materials.
Figure 3:
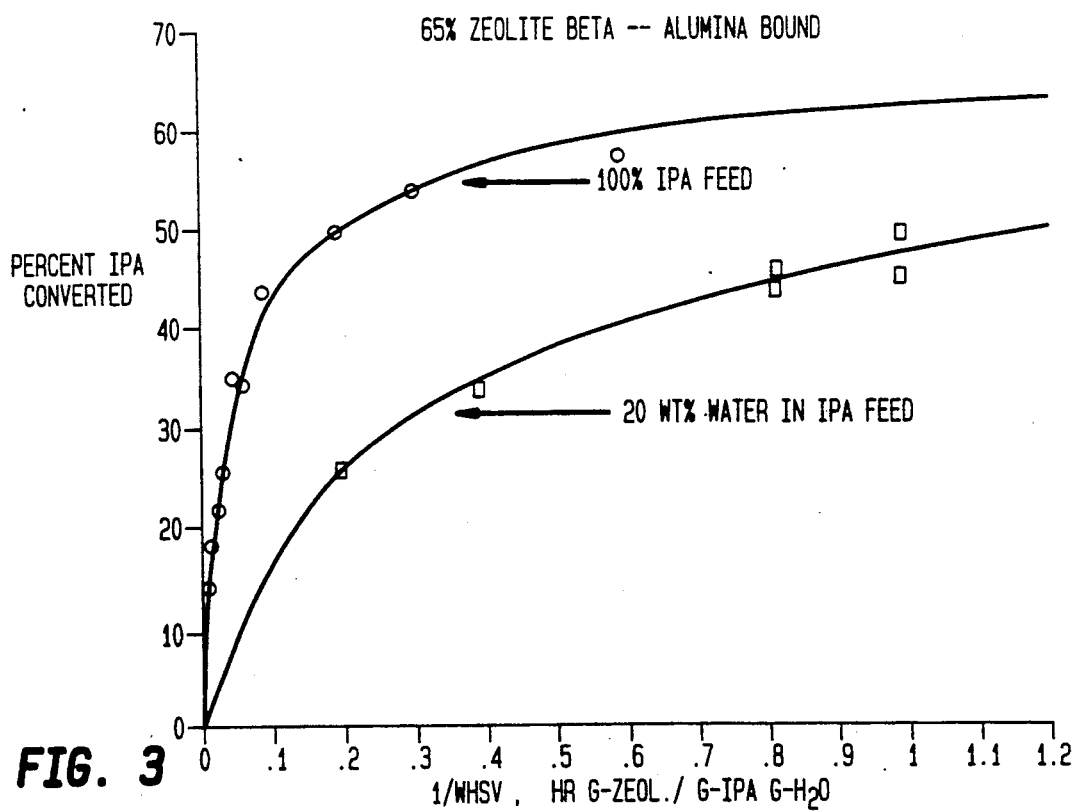

A series of experiments was conducted in a fixed bed isothermal tubular reactor with continuous liquid feed at 160° C. In FIGS. 2 and 3 IPA conversion is plotted vs reciprocal space velocity (1/WHSV), based on weight of zeolite per hourly weight of feed. When viewing the 5 curves, it is found that the approach to equilibrium is achieved much faster for the 100% pure IPA feed. In FIG. 2 the 100% IPA runs reach 30-90% approach to equilibrium at a space velocity less than 5. FIG. 2 shows that when a self-bound Beta catalyst is used, 15 weight percent (wt %) water in the feed reduced activity by a factor of about 4, as compared to pure IPA. For example, to acheive 45% IPA conversion a contact time of only 0.038 hours was required at high space velocity. But, when 15% water was cofed, a contact time of 0.16 hours was needed for the same 40% conversion rate - about 4.2 times longer. In FIG. 3 comparison was made between pure IPA and feed containing 20% water, employing a standard alumina-bound zeolite Beta (65%) extrudate catalyst. In these runs 40% conversion is acheived at 0.57 and 0.077 hours for the 20%-80% water-IPA mixtue and pure IPA, respectively. This is interpreted as a seven-fold difference in activity between these feeds. Accordingly, it is considered very advantageous to remove water to the extent that is economically feasible prior to the IPA conversion to DIPE.

Figure 4:
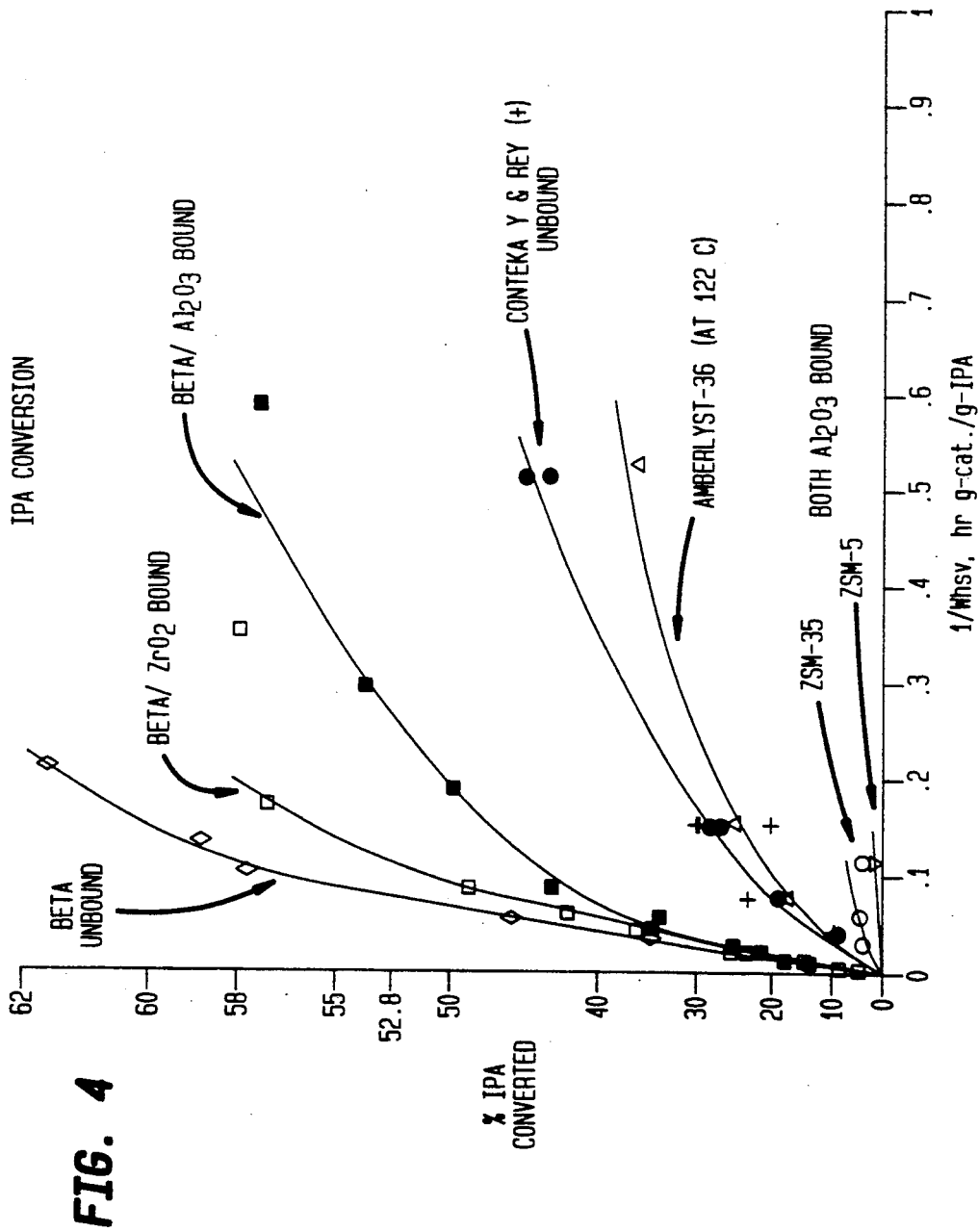

In FIG. 4, conversion of IPA with various catalysts is depicted graphically, corresponding to the following examples. These data show the unusually high activity of zeolite Beta and various Beta extrudates for the conversion of isopropyl alcohol (IPA) to diisopropyl ether (DIPE) compared to the Conteka Y, dealuminized REY, ZSM-35, ZSM-5, and a resin catalyst. Resin catalyst (Amberlyst-36) was tested at 122° C., its upper temperature limit recommended by the manufacturer, while all other test were conducted at about 160° C. FIG. 4 clearly shows the superiority of Beta catalysts.

Example 1 - Zeolite Beta Catalyst (TEA crystal pelleted, sized 14/60 mesh, acid exchanged, calcined without binder

| RUN. ID | 1.01 | 1.02 | 1.03 | 1.04 | 1.05 |
|---|---|---|---|---|---|
| HR ON STREAM | 4 | 5 | 22 | 27 | 30 |
| TEMPERATURE, °C. | 160 | 160 | 161 | 161 | 160 |
| PRESSURE, PSI | 1050 | 1050 | 1010 | 1010 | 1040 |
| FEED [C/O] | 3.00 | 3.00 | 3.00 | 3.00 | 3.00 |
| WHSV IPA/Zeol. | 9.55 | 18.13 | 0.95 | 2.40 | 4.71 |
| CONVERSION PCT | 57.77 | 46.37 | 65.87 | 63.47 | 61.69 |
| PRODUCT COMPOSITION, WT PCT | | | | | |
| WATER | 11.4 | 8.5 | 10.3 | 13.3 | 10.9 |
| C=CC | 7.5 | 5.8 | 11.8 | 9.2 | 8.4 |
| IPA | 41.7 | 53.5 | 35.0 | 35.8 | 38.4 |
| DIPE | 39.3 | 32.2 | 41.9 | 41.3 | 42.2 |
| C-6 | 0.1 | 0.0 | 1.0 | 0.4 | 0.1 |
| EXIT [C/O] | 2.88 | 2.97 | 3.27 | 2.81 | 3.02 |
| ERROR MB WT PCT | −5.8 | 1.0 | 5.4 | 1.5 | −0.7 |
| RUN. ID | 1.06 | 1.07 | 1.08 | 1.09 | 1.10 |
| HR ON STREAM | 47 | 51 | 52 | 71 | 78 |
| TEMPERATURE, | 162 | 161 | 162 | 162 | 161 |
| PRESSURE, PSI | 1010 | 1040 | 1050 | 1040 | 1040 |
| FEED [C/O] | 3.00 | 3.00 | 3.00 | 3.00 | 3.00 |
| WHSV IPA/Zeol. | 0.48 | 7.35 | 29.03 | 1.35 | 3.57 |
| CONVERSION PCT | 64.54 | 58.87 | 35.17 | 65.51 | 62.97 |
| PRODUCT COMPOSITION, WT PCT | | | | | |
| WATER | 10.9 | 11.8 | 6.4 | 11.5 | 13.2 |
| C=CC | 8.6 | 7.8 | 4.2 | 11.7 | 9.2 |
| IPA | 35.8 | 40.5 | 64.7 | 34.9 | 36.3 |
| DIPE | 42.4 | 39.8 | 24.7 | 41.2 | 41.0 |
| C-6 | 2.1 | 0.1 | 0.0 | 0.7 | 0.2 |
| EXIT [C/O] | 3.13 | 2.86 | 2.98 | 3.12 | 2.82 |
| ERROR MB WT PCT | 12.3 | 0.8 | 0.4 | −0.1 | −1.5 |

Example 2 - Zeolite Beta Catalyst/ZrO2 Bound (1/16" Extrudate)

| RUN. ID | 2.01 | 2.02 | 2.03 | 2.04 | 2.05 | 2.06 |
|---|---|---|---|---|---|---|
| HR ON STREAM | 3 | 19 | 23 | 26 | 27 | 28 |
| TEMPERATURE, | 161 | 161 | 161 | 161 | 161 | 161 |
| PRESSURE, PSI | 1000 | 1000 | 1000 | 1000 | 1000 | 1000 |
| FEED [C/O] | 3.00 | 3.00 | 3.00 | 3.00 | 3.00 | 3.00 |
| WHSV IPA/Zeol. | 16.58 | 2.82 | 5.79 | 11.46 | 23.20 | 44.47 |
| CONVERSION PCT | 42.43 | 57.92 | 57.16 | 48.93 | 36.62 | 25.84 |
| PRODUCT COMPOSITION, WT PCT | | | | | | |
| WATER | 7.8 | 11.7 | 10.9 | 9.0 | 6.4 | 4.3 |
| C=CC | 4.9 | 8.8 | 8.2 | 5.9 | 4.1 | 3.2 |
| IPA | 57.3 | 41.6 | 42.6 | 50.8 | 63.4 | 74.3 |
| DIPE | 29.9 | 37.6 | 38.2 | 34.2 | 26.1 | 18.1 |
| C-6 | 0.0 | 0.3 | 0.1 | 0.0 | 0.0 | 0.0 |
| EXIT [C/O] | 2.96 | 2.89 | 2.94 | 2.95 | 3.00 | 3.02 |
| ERROR MB WT PCT | −2.3 | 2.9 | 5.2 | 2.8 | 0.4 | −4.6 |
| Ex. 2A Beta/ZrO2 | | | | | | |
| HR ON STREAM | 3 | 5 | 22 | 26 | 29 | 30 |
| TEMPERATURE, | 161 | 161 | 162 | 162 | 161 | 161 |
| PRESSURE, PSI | 1000 | 1000 | 1000 | 1000 | 1000 | 1000 |
| FEED [C/O] | 3.00 | 3.00 | 3.00 | 3.00 | 3.00 | 3.00 |
| WHSV IPA/Zeol. | 132.69 | 177.52 | 22.41 | 45.94 | 89.12 | 352.80 |
| CONVERSION PCT | 11.06 | 8.67 | 35.32 | 23.64 | 15.04 | 5.01 |
| PRODUCT COMPOSITION, WT PCT | | | | | | |
| WATER | 1.6 | 1.3 | 5.5 | 3.9 | 2.4 | 0.8 |
| C=CC | 1.6 | 1.2 | 5.3 | 2.7 | 1.6 | 0.7 |
| IPA | 89.3 | 91.5 | 65.3 | 76.5 | 85.1 | 95.1 |
| DIPE | 7.5 | 5.9 | 23.9 | 16.9 | 10.9 | 3.4 |
| C-6 | 0.0 | 0.0 | 0.0 | 0.0 | 0.0 | 0.0 |
| EXIT [C/O] | 3.04 | 3.02 | 3.10 | 3.02 | 3.02 | 3.01 |
| ERROR MB WT PCT | −2.8 | −1.6 | −0.9 | 4.7 | 3.8 | 2.8 |

Example 3 - Zeolite Beta Catalyst/Al2O3 Bound 1/16" Extrudate

| HR ON STREAM | 5 | 6 | 6 | 25 | 28 | 31 | 49 |
|---|---|---|---|---|---|---|---|
| TEMPERATURE, | 160 | 162 | 160 | 162 | 162 | 160 | 160 |
| PRESSURE, PSI | 1000 | 1000 | 1000 | 1000 | 1000 | 1000 | 1000 |
| FEED [C/O] | 3.00 | 3.00 | 3.00 | 3.00 | 3.00 | 3.00 | 3.00 |
| WHSV IPA/Zeol. | 11.57 | 21.69 | 42.62 | 1.69 | 3.36 | 5.28 | 0.68 |
| CONVERSION PCT | 43.70 | 35.00 | 21.79 | 57.38 | 53.90 | 49.84 | 63.36 |
| PRODUCT COMPOSITION, WT PCT | | | | | | | |
| WATER | 7.6 | 6.1 | 3.4 | 11.3 | 10.5 | 9.5 | 10.9 |
| C=CC | 6.1 | 4.2 | 2.3 | 7.7 | 5.9 | 5.6 | 9.6 |
| IPA | 56.5 | 65.1 | 78.5 | 42.1 | 45.5 | 49.7 | 36.9 |
| DIPE | 29.8 | 24.6 | 15.8 | 38.7 | 38.1 | 35.2 | 42.1 |
| C-6 | 0.0 | 0.0 | 0.0 | 0.2 | 0.0 | 0.0 | 0.4 |
| EXIT [C/O] | 3.03 | 3.01 | 3.04 | 2.89 | 2.88 | 2.91 | 3.09 |
| ERROR MB WT PCT | 0.6 | 4.9 | 1.0 | 7.5 | 0.8 | 5.8 | 2.5 |

Example 4 - Zeolite Beta/Al2O3 Bound 1/16" Extrudate

| RUN. ID | 4.01 | 4.02 | 4.03 | 4.04 | 4.05 |
|---|---|---|---|---|---|
| HR ON STREAM | 1 | 17 | 19 | 22 | 33 |
| TEMPERATURE, | 161 | 161 | 161 | 161 | 159 |
| PRESSURE, PSI | 1000 | 1000 | 1000 | 1000 | 1000 |
| FEED [C/O] | 3.00 | 3.00 | 3.00 | 3.00 | 3.00 |
| WHSV IPA/Zeol. | 23.16 | 1.37 | 1.37 | 5.04 | 2.28 |
| CONVERSION PCT | 34.00 | 60.93 | 61.02 | 52.61 | 57.16 |
| PRODUCT COMPOSITION, WT PCT | | | | | |
| WATER | 5.8 | 12.2 | 12.2 | 9.8 | 11.6 |
| C=CC | 4.9 | 8.7 | 8.8 | 6.1 | 7.4 |
| IPA | 66.2 | 38.6 | 38.5 | 47.1 | 42.1 |
| DIPE | 23.0 | 40.3 | 40.3 | 37.0 | 38.8 |
| C-6 | 0.0 | 0.2 | 0.2 | 0.0 | 0.1 |
| EXIT [C/O] | 3.04 | 2.87 | 2.88 | 2.94 | 2.84 |
| ERROR MB WT PCT | −0.8 | 0.7 | 2.7 | 0.7 | −4.3 |

Example 5 - Zeolite Y Pelleted/Sized 20/60 M Calcined

| RUN. ID | 5.01 | 5.02 | 5.03 | 5.04 | 5.05 | 5.06 |
|---|---|---|---|---|---|---|
| HR ON STREAM | 4 | 4 | 5 | 6 | 23 | 2 |
| TEMPERATURE, | 161 | 161 | 162 | 162 | 162 | 162 |
| PRESSURE, PSI | 1000 | 1000 | 1000 | 1000 | 1000 | 1000 |
| FEED [C/O] | 3.00 | 3.00 | 3.00 | 3.00 | 3.00 | 3.00 |
| WHSV IPA/Zeol. | 6.63 | 6.63 | 12.83 | 25.73 | 1.94 | 1.94 |
| CONVERSION PCT | 28.47 | 27.00 | 18.95 | 8.81 | 43.80 | 45.38 |
| PRODUCT COMPOSITION, WT PCT | | | | | | |
| WATER | 5.1 | 4.9 | 3.1 | 0 | 8.4 | 8.3 |
| C=CC | 3.0 | 1.9 | 2.4 | 1.0 | 3.4 | 4.5 |
| IPA | 71.4 | 72.6 | 81.2 | 92.6 | 55.6 | 54.3 |
| DIPE | 20.6 | 20.5 | 13.2 | 6.4 | 32.7 | 32.9 |
| C-6 | 0.0 | 0.0 | 0.0 | 0.0 | 0.0 | 0.0 |
| EXIT [C/O] | 2.98 | 2.95 | 3.02 | 3.16 | 2.89 | 2.94 |
| ERROR MB WT PCT | 2.5 | −2.2 | −1.1 | −0.4 | 1.8 | −0.6 |

Example 6 - Zeolite REY (Dealuminized 30:1 Si:Al Pelleted/Sized 20/60 M Calcined

| RUN. ID | 6.01 | 6.02 | 6.03 | 6.04 | 6.05 | 6.06 | 6.07 |
|---|---|---|---|---|---|---|---|
| HR ON STREAM | 4 | 5 | 6 | 23 | 25 | 28 | 29 |
| TEMPERATURE, | 161 | 161 | 161 | 161 | 161 | 161 | 161 |
| PRESSURE, PSI | 1000 | 1000 | 1000 | 1000 | 1000 | 1000 | 1000 |
| FEED [C/O] | 3.00 | 3.00 | 3.00 | 3.00 | 3.00 | 3.00 | 3.00 |
| WHSV IPA/Zeol. | 6.55 | 6.55 | 13.18 | 0.80 | 0.80 | 6.55 | 24.19 |
| CONVERSION PCT | 30.04 | 29.68 | 23.17 | 40.71 | 40.18 | 20.22 | 9.51 |
| PRODUCT COMPOSITION, WT PCT | | | | | | | |
| WATER | 6.4 | 6.2 | 4.5 | 8.0 | 9.1 | 4.2 | 1.9 |
| C=CC | 7.0 | 6.6 | 5.5 | 11.1 | 9.6 | 4.6 | 2.2 |
| IPA | 69.7 | 70.0 | 76.9 | 59.6 | 59.2 | 79.6 | 90.5 |
| DIPE | 16.9 | 17.1 | 13.1 | 21.3 | 22.1 | 11.5 | 5.4 |
| C-6 | 0.0 | 0.0 | 0.0 | 0.0 | 0.0 | 0.0 | 0.0 |
| EXIT [C/O] | 2.96 | 2.96 | 3.02 | 3.05 | 2.89 | 2.98 | 3.00 |
| ERROR MB WT PCT | 0.5 | −0.5 | −1.2 | 0.9 | −0.4 | 1.5 | −0.6 |

Example 7 - AMBERLYST-36 Polysulfonic acid resin (MEOH WASHED/Dried 120 C)

| RUN. ID | 7.02 | 7.03 | 7.04 | 7.05 | 7.06 |
|---|---|---|---|---|---|
| HR ON STREAM | 4 | 6 | 25 | 26 | 29 |
| TEMPERATURE, | 120 | 121 | 122 | 122 | 122 |
| PRESSURE, PSI | 1000 | 1000 | 1000 | 1000 | 1000 |
| FEED [C/O] | 3.00 | 3.00 | 3.00 | 3.00 | 3.00 |
| WHSV IPA/Catalyst | 6.46 | 13.02 | 0.80 | 0.80 | 1.90 |
| CONVERSION PCT | 25.59 | 18.13 | 41.90 | 39.15 | 36.56 |

-continued

| RUN. ID | 7.02 | 7.03 | 7.04 | 7.05 | 7.06 |
|---|---|---|---|---|---|
| PRODUCT COMPOSITION, WT PCT | | | | | |
| WATER | 4.8 | 3.3 | 7.1 | 9.5 | 8.7 |
| C=CC | 7.5 | 5.4 | 5.8 | 3.0 | 8.1 |
| IPA | 74.9 | 82.3 | 58.4 | 59.0 | 62.5 |
| DIPE | 12.8 | 8.9 | 28.7 | 28.6 | 20.8 |
| C-6 | 0.0 | 0.0 | 0.0 | 0.0 | 0.0 |
| EXIT [C/O] | 3.07 | 3.06 | 3.05 | 2.71 | 2.85 |
| ERROR MB WT PCT | −1.0 | 3.5 | 15.3 | 7.6 | 0.7 |

Example 8 - Zeolite ZSM-35/Al2O3 Bound 1/16" Extrudate

| RUN. ID | 8.01 | 8.02 | 8.03 |
|---|---|---|---|
| HR ON STREAM | 3 | 4 | 7 |
| TEMPERATURE, | 161 | 161 | 161 |
| FEED [C/O] | 3.00 | 3.00 | 3.00 |
| WHSV IPA/Zeol. | 17.01 | 34.27 | 8.72 |
| CONVERSION PCT | 4.81 | 4.06 | 4.13 |
| PRODUCT COMPOSITION, WT PCT | | | |
| WATER | 2.1 | 0.0 | 2.7 |
| C=CC | 3.0 | 2.8 | 2.6 |
| IPA | 94.5 | 97.1 | 94.4 |
| DIPE | 0.4 | 0.1 | 0.3 |
| C-6 | 0.0 | 0.0 | 0.0 |
| EXIT [C/O] | 2.93 | 3.12 | 2.86 |
| ERROR MB WT PCT | 3.2 | 2.4 | 6.9 |

Example 9 - Zeolite ZSM-5/Self-Bound 14/30 Mesh

| RUN. ID | 9.01 | 9.03 |
|---|---|---|
| HR ON STREAM | 4 | 21 |
| TEMPERATURE, | 162 | 161 |
| PRESSURE, PSI | 1000 | 1000 |
| FEED [C/O] | 3.00 | 3.00 |
| WHSV IPA/Zeolite | 8.82 | 0.43 |
| CONVERSION PCT | 1.33 | 3.70 |
| PRODUCT COMPOSITION, WT PCT | | |
| WATER | 0.2 | 0.9 |
| C=CC | 0.3 | 0.0 |
| IPA | 98.8 | 96.0 |
| DIPE | 0.6 | 3.1 |
| C-6 | 0.2 | 0.0 |
| EXIT [C/O] | 3.01 | 2.96 |
| ERROR MB WT PCT | −1.5 | −22.6 |

While the invention has been described by specific examples and embodiments, there is no intent to limit the inventive concept except as set forth in the following claims.

We claim:

1. An integrated continuous process for the production of diisopropyl ether and substantially pure propene from a mixed aliphatic feedstock containing propene and propane, comprising the steps of:
   a) contacting the aliphatic feedstock and water in a first reaction zone with acidic olefin hydration catalyst under olefins hydration conditions whereby an effluent stream containing isopropanol and unreacted aliphatic hydrocarbon is produced substantially free of di-isopropyl ether;
   b) separating the first reaction zone effluent stream to recover unreacted hydrocarbon and an oxygenate stream comprising isopropanol;
   c) contacting said isopropanol oxygenate stream with a zeolite acidic etherification catalyst in a second reaction zone under etherification conditions to produce an etherification effluent stream containing di-isopropyl ether, water and propene; and
   d) fractionating the etherification effluent stream to produce a substantially pure propene product stream and an ether product stream.

2. The process of claim 1 including a fractionation step for separating a $C_3$- unreacted hydrocarbon overhead fraction from an isopropanol-rich aqueous bottoms stream and further fractionating said isopropanol-rich aqueous stream to provide an azeotropic mixture consisting essentially of about 85 wt % isopropanol and about 15 wt % water.

3. The process of claim 1 wherein said etherification catalyst comprises acidic shape selective medium pore zeolite.

4. The process of claim 3 wherein said etherification catalyst consists essentially of zeolite Beta.

5. The process of claim 1 wherein said hydration catalyst comprises zeolite ZSM-5 or polysulfonic acid resin and produces oxygenate consisting essentially of substantially pure isopropanol.

6. The process of claim 1 wherein the first reaction zone conditions comprise temperature of about 50° to 200° C.

7. A process for production of diisopropyl ether and propene from isopropanol feed comprising:
   contacting isopropanol containing 0-20 wt % water with acidic large pore zeolite etherification catalyst under etherification conditions to convert at least 60% of the isopropanol to di-isopropyl ether, water and propene.

8. The process of claim 7 wherein the isopropanol contains not more than about 15 wt % water; wherein etherification reaction temperature is about 90°-200° C.

9. The process of claim 8 wherein isopropanol reactant consists essentially of an azeotropic mixture of about 85 wt % isopropanol and about 15 wt % water.

10. The process of claim 7 wherein said etherification catalyst comprises acidic zeolite Beta.

11. The process of claim 7 including the step of fractionating etherification reaction effluent to recover substantially pure propene.

12. A continuous process for production of diisopropyl ether and propene from isopropanol feed comprising:
   contacting an isopropanol-rich feedstream, containing at least 80% isopropanol and containing not more than 15 wt % water, with acidic etherification catalyst comprising zeolite Beta under etherificaton conditions at reaction temperature of about 90°-200° C. to convert isopropanol to di-isopropyl ether, water and propene with about 30 to 90% approach to equilibrium.

13. The process of claim 12 wherein said etherification catalyst consists essentially of acidic aluminosilicate zeolite Beta having a silica:alumina ratio of about 30:1 to 50:1 and alpha value of about 200 to 1000; and wherein space velocity is about 10 to 20 WHSV, and reaction pressure is about 450 to 7000 kPa.

14. The process of claim 12 wherein the feedstream consists essentially of isopropanol.

15. A process for production of diisopropyl ether and propene from a mixed aliphatic hydrocarbon feedstock containing propene and propane, comprising the steps of:
   contacting the aliphatic feedstock and water in a primary reaction zone with acidic olefin hydration catalyst under olefins hydration conditions to produce an isopropanol-rich primary effluent stream;

separating the primary effluent stream to recover unreacted hydrocarbon and a substantially anhydrous stream consisting essentially of isopropanol;

contacting the substantially anhydrous isopropanol stream with acidic etherification catalyst comprising zeolite Beta in a secondary reaction zone under etherification conditions to produce an etherification effluent stream containing di-isopropyl ether, water and propene; and fractionating the etherification effluent stream to recover propene and di-isopropyl ether.

16. A process for production of diisopropyl ether and propene from isopropanol feed comprising:

contacting substantially anhydrous feed consisting essentially of isopropanol with acidic zeolite Beta catalyst at reaction temperature of about 90°–200° C.

* * * * *